US010481057B1

(12) United States Patent
Song et al.

(10) Patent No.: US 10,481,057 B1
(45) Date of Patent: Nov. 19, 2019

(54) MECHANICAL TESTING EQUIPMENT FOR MATERIAL CHARACTERIZATION

(71) Applicant: National Technology & Engineering Solutions of Sandia, LLC, Albuquerque, NM (US)

(72) Inventors: Bo Song, Albuquerque, NM (US); Evan P. Johnson, Los Lunas, NM (US); Matthew A Spletzer, Albuquerque, NM (US); Jack D. Heister, Albuquerque, NM (US); Randy L. Everett, Albuquerque, NM (US); Thomas L. Martinez, Albuquerque, NM (US); Marlene E. Knight, Albuquerque, NM (US); Dennis John Kenney, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 154 days.

(21) Appl. No.: 15/366,921

(22) Filed: Dec. 1, 2016

(51) Int. Cl.
*G01N 3/303* (2006.01)
*G01N 3/30* (2006.01)

(52) U.S. Cl.
CPC ..... *G01N 3/303* (2013.01); *G01N 2203/0033* (2013.01); *G01N 2203/0075* (2013.01)

(58) Field of Classification Search
CPC ... G01N 2203/0016; G01N 2203/0017; G01N 2203/0033; G01N 2203/0075
See application file for complete search history.

(56) References Cited

U.S. PATENT DOCUMENTS

| | | | | |
|---|---|---|---|---|
| 3,142,980 | A * | 8/1964 | Andersen | G01N 3/10 73/12.01 |
| 2002/0043099 | A1* | 4/2002 | Maruoka | G01N 3/30 73/54.39 |
| 2014/0047898 | A1* | 2/2014 | Garcia-Romeu Martinez | G01N 3/303 73/12.06 |
| 2018/0017475 | A1* | 1/2018 | Sweet | G01N 3/307 |

FOREIGN PATENT DOCUMENTS

| | | | | |
|---|---|---|---|---|
| CN | 101769837 | A * | 7/2010 | |
| EP | 520078 | A1 * | 12/1992 | |
| FR | 3001543 | A1 * | 8/2014 | ............... G01N 3/04 |
| JP | 55042031 | A * | 3/1980 | |
| JP | 2006194595 | A * | 7/2006 | |

(Continued)

OTHER PUBLICATIONS

REL, Inc. Sure-Flat Testing Platform brochure.
(Continued)

*Primary Examiner* — Judy Nguyen
*Assistant Examiner* — Ruben C Parco, Jr.
(74) *Attorney, Agent, or Firm* — Yee & Associates, P.C.; Gregory M. Doudnikoff

(57) ABSTRACT

A mechanical testing apparatus for a specimen is presented. The mechanical testing apparatus comprises a drop table system and a Hopkinson bar. The drop table system has a drop carriage. The Hopkinson bar is positioned parallel to a motion of the drop carriage and connected to the drop table system by the specimen.

13 Claims, 9 Drawing Sheets

(56) References Cited

FOREIGN PATENT DOCUMENTS

KR          2009053485 A  *  5/2009  ............... G01N 3/10

OTHER PUBLICATIONS

Song, B. et al, "Dynamic Tensile Characterization of a 4330-V Steel with Kolsky Bar Techniques", Proceedings of the IMPLAST 2010 Conference, Providence, RI.
Chen, W et al., "Split Hopkinson (Kolsky) Bar, Design, Testing and Applications", Mechanical Engineering Series, DOI 10.1007/978-1-4419-7982-7_1, Springer New York (2011).
Nie, X. et al., A Novel Splitting-Beam Laser Extensometer Technique for Kolsky Tension Bar Experiment, Journal of Dynamic Behavior of Materials, 1:70-74DOI 10.1007/240870-015-0005-7 (2015).

* cited by examiner

MECHANICAL TESTING EQUIPMENT FOR MATERIAL CHARACTERIZATION

GOVERNMENT LICENSE RIGHTS

This invention was made with United States Government support under Contract No. DE-AC04-94AL85000 between Sandia Corporation and the United States Department of Energy. The United States Government has certain rights in this invention.

BACKGROUND INFORMATION

1. Field

The present disclosure relates generally to mechanical testing of materials, and more specifically, to obtaining stress-strain data. Yet more specifically, the present disclosure includes a mechanical testing apparatus that may obtain mechanical property characterization of materials at intermediate strain rates.

2. Background

Conventional mechanical testing apparatuses are limited in the strain rate for material characterization. Conventional mechanical testing apparatuses may perform mechanical testing at either low or high strain rates. For example, a conventional servohydraulic testing apparatus may be used to perform mechanical testing at low strain rates below $10^1$ $s^{-1}$. A split Hopkinson bar may be used to perform mechanical testing at high strain rates on the order of $10^3$ $s^{-1}$ or above. Neither the conventional servohydraulic testing apparatus nor the split Hopkinson bar may be used to perform mechanical testing at intermediate strain rates on the order of $10^2$ $s^{-1}$.

SUMMARY

In one illustrative embodiment, a mechanical testing apparatus for a specimen is presented. The mechanical testing apparatus comprises a drop table system and a Hopkinson bar. The drop table system has a drop carriage. The Hopkinson bar is positioned parallel to a motion of the drop carriage and connected to the drop table system by the specimen.

In another illustrative embodiment, a mechanical testing apparatus for a specimen is presented. The apparatus comprises an impact plate, a carriage, an impactor, an accelerometer, a bar, and a number of strain gauges. The impact plate has a threaded hole configured to hold a first end of the specimen. The carriage is configured to move towards the impact plate. The impactor is connected to the carriage and configured to strike the impact plate. The accelerometer is connected to the impact plate. The bar has a threaded hole to hold a second end of the specimen. The bar is perpendicular to the impact plate. The number of strain gauges is connected to the surface of the bar.

In yet another illustrative embodiment, a method for mechanically testing a specimen is presented. A load is applied to the specimen using a drop carriage of a drop table system, wherein the specimen connects the drop table system to a Hopkinson bar, and wherein the Hopkinson bar is positioned parallel to a motion of the drop carriage.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account that conventional mechanical testing apparatuses do not perform testing for intermediate strain rates on the order of $10^2$ $s^{-1}$. Conventional mechanical testing apparatuses have an undesirable level of noise to signal in intermediate strain rates. The illustrative embodiments present a mechanical testing apparatus to perform testing for intermediate strain rates on the order of $10^2$ $s^{-1}$.

Further, the illustrative embodiments recognize and take into account that, mechanical testing apparatuses may be undesirably large. Thus, the illustrative embodiments recognize and take into account that it may be desirable for a single mechanical testing apparatus to perform mechanical testing at multiple orders of strain rates. The illustrative embodiments present a mechanical testing apparatus that may perform mechanical testing at any of high, intermediate, or low strain rates.

Figure 1:
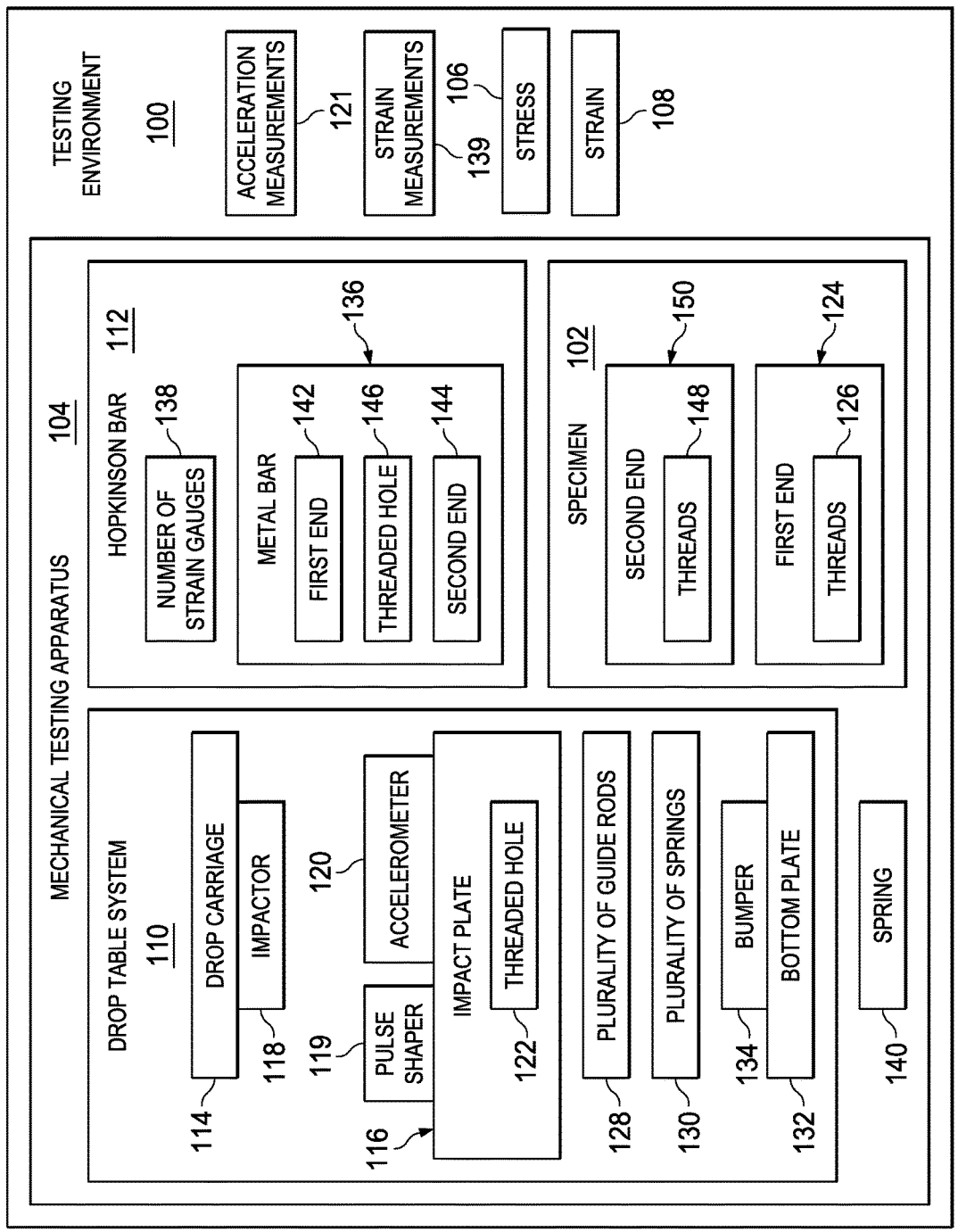
FIG. 1 is an illustration of a block diagram of a testing environment in accordance with an illustrative embodiment.

Referring now to the figures, and in particular, with reference to FIG. 1, an illustration of a block diagram of a testing environment is depicted in accordance with an illustrative embodiment. Testing environment 100 is an environment for mechanical testing of specimen 102. Mechanical testing apparatus 104 is used to determine at least one of stress 106 or strain 108 of specimen 102. Mechanical testing apparatus 104 is configured to obtain tensile stress-strain response of specimen 102 at intermediate strain rates in the order of $10^2$ s$^{-1}$.

As used herein, the phrase "at least one of," when used with a list of items, means different combinations of one or more of the listed items may be used, and only one of each item in the list may be needed. In other words, "at least one of" means any combination of items or number of items may be used from the list, but not all of the items in the list are required. The item may be a particular object, a thing, or a category.

For example, "at least one of item A, item B, or item C" may include, without limitation, item A, item A and item B, or item B. This example also may include item A, item B, and item C or item B and item C. Of course, any combination of these items may be present. In other examples, "at least one of" may be, for example, without limitation, two of item A, one of item B, and ten of item C; four of item B and seven of item C; or other suitable combinations.

Mechanical testing apparatus 104 comprises drop table system 110 and Hopkinson bar 112. Drop table system 110 has drop carriage 114. Hopkinson bar 112 is positioned parallel to a motion of drop carriage 114 and is connected to drop table system 110 by specimen 102. Mechanical testing apparatus 104 is configured to obtain a tensile stress-strain response at higher or lower strain rates by varying an impact speed of drop carriage 114 of drop table system 110.

Specimen 102 has a threaded engagement with each of drop table system 110 and Hopkinson bar 112. Drop table system 110 comprises impact plate 116, impactor 118, and accelerometer 120.

Impact plate 116 has threaded hole 122 configured to hold first end 124 of specimen 102. More specifically, threads 126 of first end 124 retain specimen 102 within threaded hole 122 of drop table system 110. Threaded hole 122 may have any desirable number or size of threads.

Drop carriage 114 is configured to move towards impact plate 116. Impactor 118 is connected to drop carriage 114. Impactor 118 is configured to strike pulse shaper 119 associated with impact plate 116.

When one component is "associated" with another component, the association is a physical association in the depicted examples. For example, a first component may be considered to be associated with a second component by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

Accelerometer 120 is connected to impact plate 116. Accelerometer 120 generates acceleration measurements 121 during operation of drop table system 110.

Drop table system 110 also comprises plurality of guide rods 128, plurality of springs 130, bottom plate 132, and bumper 134. Plurality of guide rods 128 extend through impact plate 116. Plurality of springs 130 surround each of plurality of guide rods 128. Bottom plate 132 is connected to plurality of guide rods 128. Bumper 134 is connected to bottom plate 132. Bumper 134 is configured to absorb momentum and stop impact plate 116.

Hopkinson bar 112 comprises metal bar 136 and number of strain gauges 138 connected to the surface of metal bar 136. Number of strain gauges 138 generates strain measurements 139 of metal bar 136 during testing. In some illustrative examples, strain measurements 139 of metal bar 136 may be referred to as bar strain. As used herein, "a number of" when used with reference to items means one or more items. Thus, number of strain gauges 138 is one or more strain gauges.

Metal bar 136 is suspended by spring 140 attached to first end 142 of metal bar 136. Second end 144 of metal bar 136 has threaded hole 146. Threads 148 of second end 150 of specimen 102 engage threaded hole 146 to retain specimen 102 within threaded hole 146.

Drop table system 110 is used to generate an impact by a free drop of drop carriage 114. In some illustrative examples, drop table system 110 may further include an acceleration mechanism, such as a bungee cord, a spring, or other device to impart additional force to drop carriage 114.

Impactor 118 is attached to the bottom of drop carriage 114 to strike pulse shaper 119 associated with impact plate 116. Pulse shaper 119 may be formed from any desirable material. Further, pulse shaper 119 may have any desirable size or shape. By changing at least one of the size, shape, or material of pulse shaper 119, the force applied to impact plate 116 is varied. Pulse shaper 119 is designed to generate a desired load profile to specimen 102 such that specimen 102 is deformed at a nearly constant strain rate and under stress equilibrium.

Drop table system 110 is configured such that pulse shaper 119 may be positioned on any desirable location of impact plate 116. Thus, impactor 118 may apply force to any desirable location of impact plate 116. A center point of pulse shaper 119 is desirably aligned with a center line of impactor 118. In some illustrative examples, pulse shaper 119 may be centered on impact plate 116. In these illustrative examples, impactor 118 impacts pulse shaper 119 associated with the center of the face of impact plate 116 directed towards impactor 118.

The thickness of impact plate 116 affects the bending wave within impact plate 116 generated by impactor 118. Increasing the thickness of impact plate 116 reduces the bending of impact plate 116. In some illustrative examples, impact plate 116 has a thickness of at least one inch to reduce the bending wave in impact plate 116 generated by impactor 118. In other illustrative examples, impact plate 116 has a thickness of greater than one inch. For example, in some implementations impact plate 116 may have a thickness greater than or equal to two inches.

Impact plate 116 is formed from any desirable material. The material for impact plate 116 is selected to substantially retain its shape with repeated applied force from impactor 118. As one non-limiting example, impact plate 116 may be created from hardened 4340 steel.

Plurality of guide rods 128 are associated with impact plate 116 to guide the whole of impact plate 116 to move downwards with a reduced bending effect. Changing a quantity of guide rods in plurality of guide rods 128 may affect the bending effect experienced by impact plate 116. For example, increasing the quantity of guide rods in plurality of guide rods 128 may reduce the bending experience by impact plate 116.

In some illustrative examples, plurality of guide rods 128 is four guide rods. In other illustrative examples, plurality of guide rods 128 is six guide rods. In yet other illustrative examples, plurality of guide rods 128 has greater than six guide rods.

Plurality of springs 130 are installed surrounding plurality of guide rods 128 and between impact plate 116 and bottom plate 132. Plurality of springs 130 supports impact plate 116. Plurality of springs 130 absorbs momentum provided by impactor 118 to impact plate 116. Bumper 134 installed on bottom plate 132, absorbs additional momentum and stops impact plate 116.

During operation, drop carriage 114 falls towards impact plate 116. Impactor 118 attached to the bottom of drop carriage 114 impacts pulse shaper 119 associated with impact plate 116. Impact plate 116 then transfers the impact load to specimen 102, attached to impact plate 116 through threads 126. The impact load subjects specimen 102 to dynamic tension. The tensile stress wave then transmits into the Hopkinson bar 112 through threads 148 between specimen 102 and second end 144 of metal bar 136. Number of strain gauges 138 on the surface of metal bar 136 record the whole load history applied to specimen 102. Stress 106 of specimen 102 is calculated as $$\sigma(t) = \frac{A_0}{A_S} E_0 \varepsilon_0(t) \qquad (1)$$

wherein $A_0$ is a cross-sectional area of metal bar 136; wherein $A_s$ is a cross-sectional area of specimen 102; $E_0$ is Young's modulus of Hopkinson bar 112; and $\varepsilon_0$ is strain measurements 139 of metal bar 136 recorded with number of strain gauges 138.

Accelerometer 120 is installed along the impact direction on the edge of impact plate 116 to record acceleration measurements 121 of acceleration that puts specimen 102 in tension. The integration of the acceleration history yields the impact speed on specimen 102. Therefore, the strain rate in specimen 102 can be calculated as $$\dot{\varepsilon}(t) = \frac{\int_0^t a(t)\,dt - C_0 \varepsilon_0(t)}{L_s} \qquad (2)$$

wherein $a(t)$ is the acceleration history recorded by accelerometer 120; $C_0$ is the speed of elastic stress wave in the material of metal bar 136, wherein $$C_0 = \sqrt{\frac{E_0}{\rho_0}} \qquad (3)$$

wherein $\beta_0$ is the density of the material of metal bar 136; and $L_s$ is gauge length of specimen 102. Strain 108 of specimen 102 may be determined by integrating equation 2.

$$\varepsilon(t) = \int_0^t \dot{\varepsilon}\,dt = \int_0^t \frac{\int_0^t a(t)\,dt - C_0 \varepsilon_0(t)}{L_s}\,dt \qquad (4)$$

Equations (1) and (4) provide stress 106 and strain 108 histories for specimen 102 as a function of time. The stress-strain response of the material under investigation is obtained by synchronizing stress 106 and strain 108 histories with elimination of time.

The original height and weight of drop carriage 114 control the impact speed and subsequent strain 108 on specimen 102. The impact speed can be further increased by applying a bungee cable to accelerate drop carriage 114. In general, drop table system 110 with free fall produces impact speeds between 0.5 and 10 m/s, which can subject specimen 102 to dynamic tension at the strain rates between 50 and 1000 s$^{-1}$. The strain-rate range also depends on the material under investigation and specimen 102 geometry design.

Metal bar 136 in Hopkinson bar 112 may be used in mechanical testing apparatus 104. Metal bar 136 may be any desirable length. In one illustrative example, metal bar 136 is twelve feet long. Metal bar 136 can hold a duration of loading pulse as long as 1.4 millisecond. Therefore, mechanical testing apparatus 104 can deform specimen 102 to a maximum tensile strain between 6% to 140%, depending on the strain rate.

The illustration of testing environment 100 in FIG. 1 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, pulse shaper 119 may be present in a different location. Although pulse shaper 119 is associated with impact plate 116 as shown in FIG. 1 and described above, pulse shaper 119 may instead be associated with impactor 118.

Figure 2:
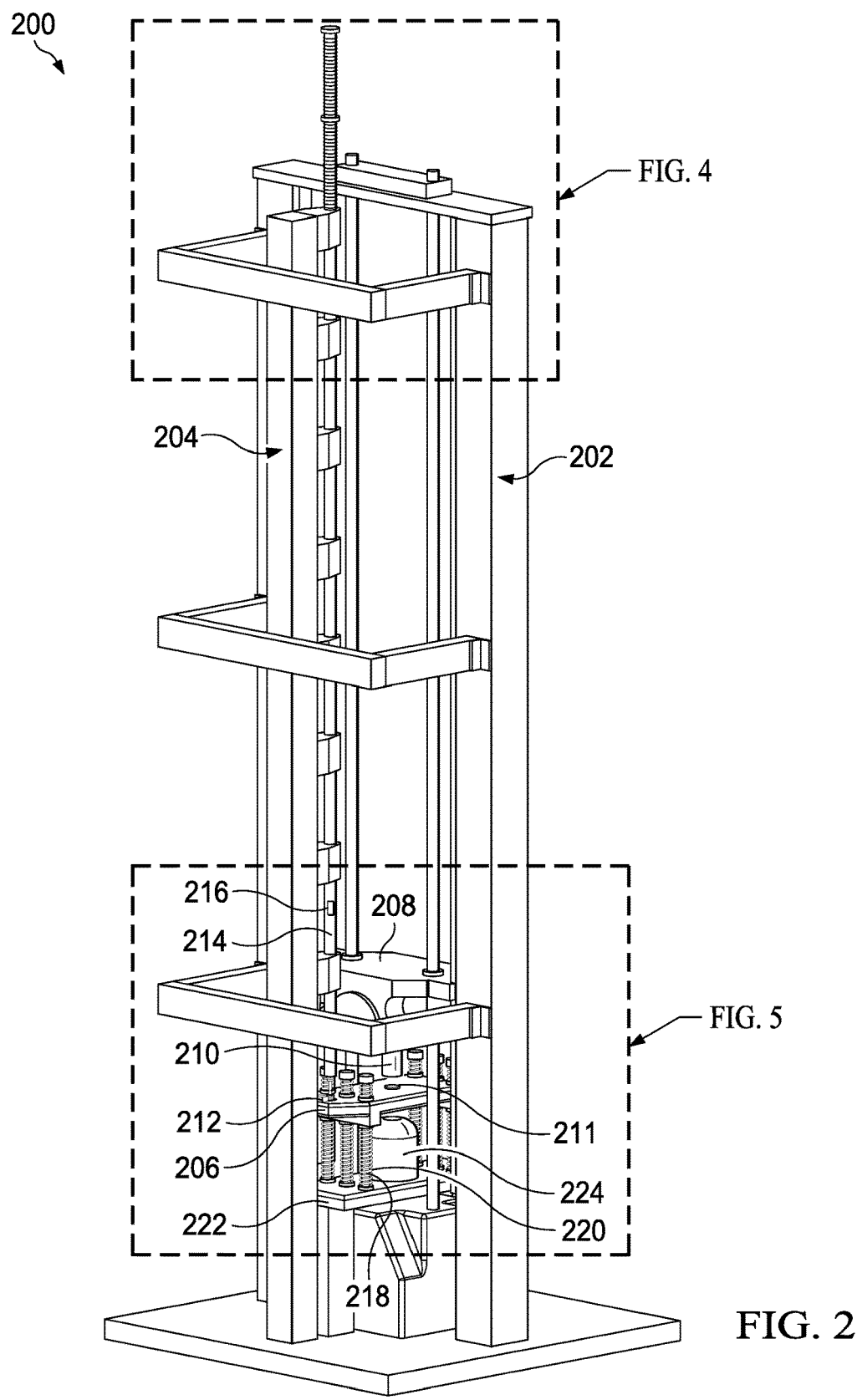
FIG. 2 is an illustration of an isometric view of a mechanical testing apparatus in accordance with an illustrative embodiment.

Turning now to FIG. 2, an illustration of an isometric view of a mechanical testing apparatus is depicted in accordance with an illustrative embodiment. Mechanical testing apparatus 200 is a physical implementation of mechanical testing apparatus 104 of FIG. 1.

Mechanical testing apparatus 200 has drop table system 202 and Hopkinson bar 204. Drop table system 202 may be a physical implementation of drop table system 110 of FIG. 1. Hopkinson bar 204 may be a physical implementation of Hopkinson bar 112 of FIG. 1. Mechanical testing apparatus 200 may be referred to as a Dropkinson bar apparatus for the novel combination of drop table system 202 and Hopkinson bar 204.

FIG. 2 shows the design of the Dropkinson bar apparatus in tension mode. Drop table system 202 is used to generate an impact load that is transferred into a tensile specimen. The impact load subjects the specimen to dynamic tension. The tensile stress wave then transmits into vertically oriented Hopkinson bar 204 through the threads between the specimen and the bar end. Number of strain gauges 216 on the surface of Hopkinson bar 204 records the whole load history applied to the specimen.

Mechanical testing apparatus 200 comprises impact plate 206, carriage 208, impactor 210, accelerometer 212, bar 214, and number of strain gauges 216. Impact plate 206 is a component of drop table system 202. Impact plate 206 may be a physical implementation of impact plate 116 of FIG. 1. A specimen to be tested would be connected to impact plate 206 and bar 214. More specifically, impact plate 206 has a threaded hole configured to hold a first end of a specimen.

Impact plate 206 may have any desirable thickness. As depicted, impact plate 206 is about two inches thick. More specifically, impact plate 206 is a two-inch thick piece of hardened 4340 steel.

Carriage 208 is a component of drop table system 202 and may be a physical implementation of drop carriage 114 of FIG. 1. Carriage 208 is configured to move towards impact plate 206. As depicted, carriage 208 is configured to free fall towards impact plate 206. In mechanical testing apparatus 200, force applied to impact plate 116 may be varied by varying the height from which carriage 208 is dropped.

In other non-depicted examples, an additional acceleration mechanism may be associated with carriage 208. In these examples, an acceleration mechanism, such as a bungee cord, a spring, or other device may impart additional force to carriage 208.

Impactor 210 is a component of drop table system 202. Impactor 210 may be a physical implementation of impactor 118 of FIG. 1. Impactor 210 is connected to carriage 208 and configured to strike pulse shaper 211, associated with impact plate 206. The characteristics of the force applied to impact plate 206 may be changed by changing at least one of the size, shape, or material of pulse shaper 211. Impactor 210 and pulse shaper 211 may be more clearly seen in FIG. 6 below.

Accelerometer 212 is a component of drop table system 202. Accelerometer 212 may be a physical implementation of accelerometer 120 of FIG. 1. Accelerometer 212 is connected to impact plate 206. Accelerometer 212 measures the acceleration of impact plate 206 due to the force imparted by impactor 210. Accelerometer 212 is more clearly seen in FIGS. 6-9.

Bar 214 is a component of Hopkinson bar 204 and may be a physical implementation of metal bar 136 of FIG. 1. Bar 214 is perpendicular to impact plate 206 and has a threaded hole to hold a second end of a specimen. Bar 214 may have any desirable diameter and any desirable length. As depicted, bar 214 has a one-inch diameter. Bar 214 may be made of any desirable high-strength metallic material. Specifically, bar 214 is formed of a metallic material having a greater strength than a sample to be tested. In some illustrative examples, bar 214 is formed of a type of steel. In some illustrative examples, bar 214 is made of MAR C300 steel where $E_0$=189.7 GPa.

Number of strain gauges 216 is connected to the surface of bar 214. Number of strain gauges 216 is configured to measure strain in bar 214 during testing of a specimen. Number of strain gauges 216 is a component of Hopkinson bar 204 and may be a physical implementation of number of strain gauges 138 of FIG. 1. Number of strain gauges 216 is more clearly seen in FIG. 7.

As depicted, mechanical testing apparatus 200 further comprises plurality of guide rods 218, plurality of springs 220, bottom plate 222, and bumper 224. Plurality of guide rods 218 extend through impact plate 206 and are configured to reduce a bending effect on impact plate 206. As depicted, Plurality of guide rods 218 includes six rods. However, plurality of guide rods 218 may include any desirable number of rods. Plurality of guide rods 218, plurality of springs 220, bottom plate 222, and bumper 224 may be more clearly seen in FIG. 5.

Plurality of springs 220 surrounds plurality of guide rods 218. Plurality of springs 220 support impact plate 206. Bottom plate 222 is connected to plurality of guide rods 218. Bumper 224 is connected to bottom plate 222 and is configured to absorb momentum and to stop impact plate 206.

Mechanical testing apparatus 200 is configured to obtain a tensile stress-strain response of a specimen at intermediate strain rates in the order of $10^2$ $s^{-1}$. Mechanical testing apparatus 200 is further configured to obtain a tensile stress-strain response at higher or lower strain rates by varying the impact speed of carriage 208 of drop table system 202.

Figure 3:
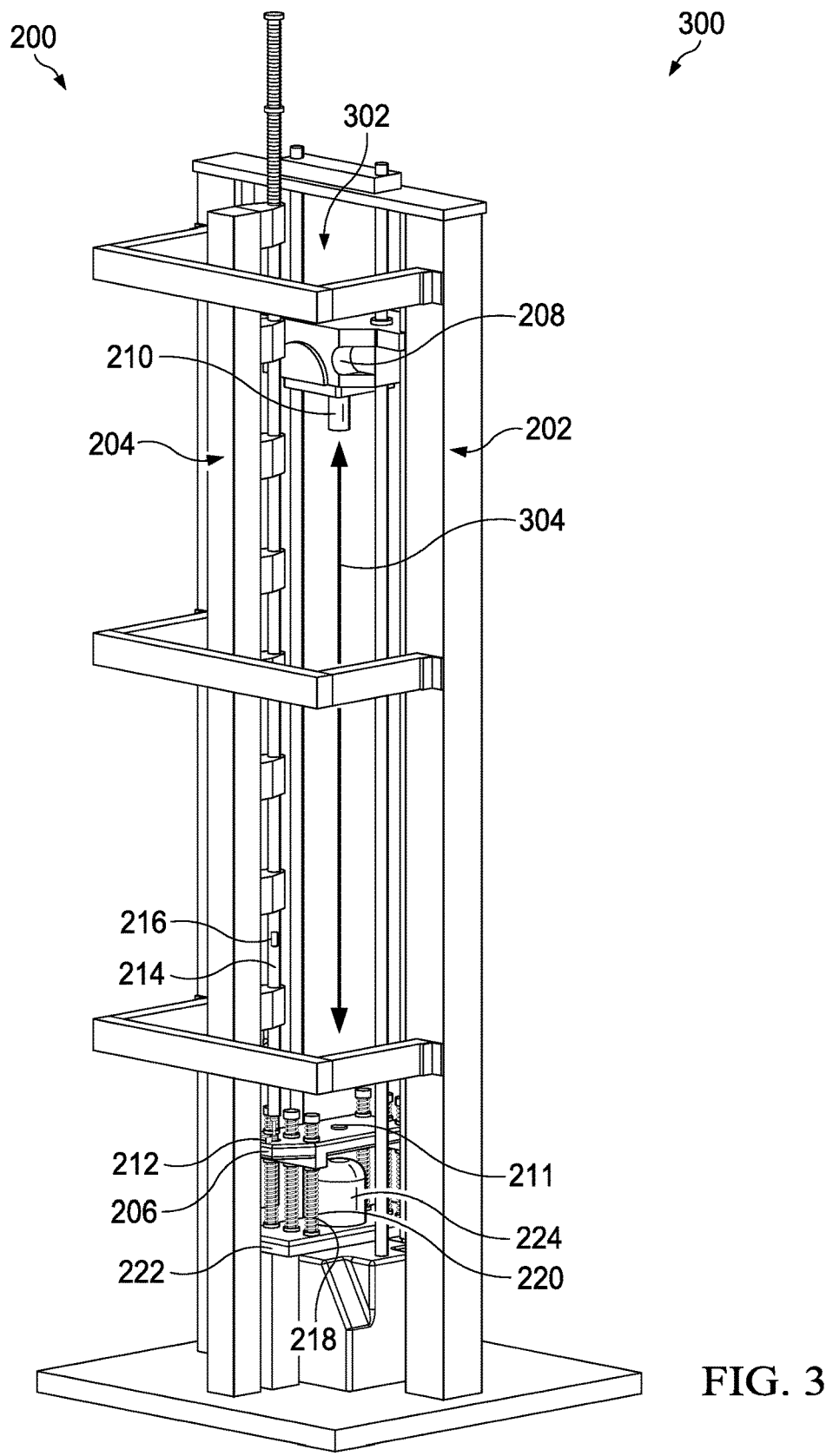
FIG. 3 is an illustration of an isometric view of a mechanical testing apparatus with a raised drop carriage in accordance with an illustrative embodiment.

Turning now to FIG. 3, an illustration of an isometric view of a mechanical testing apparatus with a raised drop carriage is depicted in accordance with an illustrative embodiment. View 300 is a view of mechanical testing apparatus 200 with carriage 208 in raised position 302. Increasing distance 304 of carriage 208 from impact plate 206, increases the force applied to impact plate 206 and to the specimen.

Figure 4:
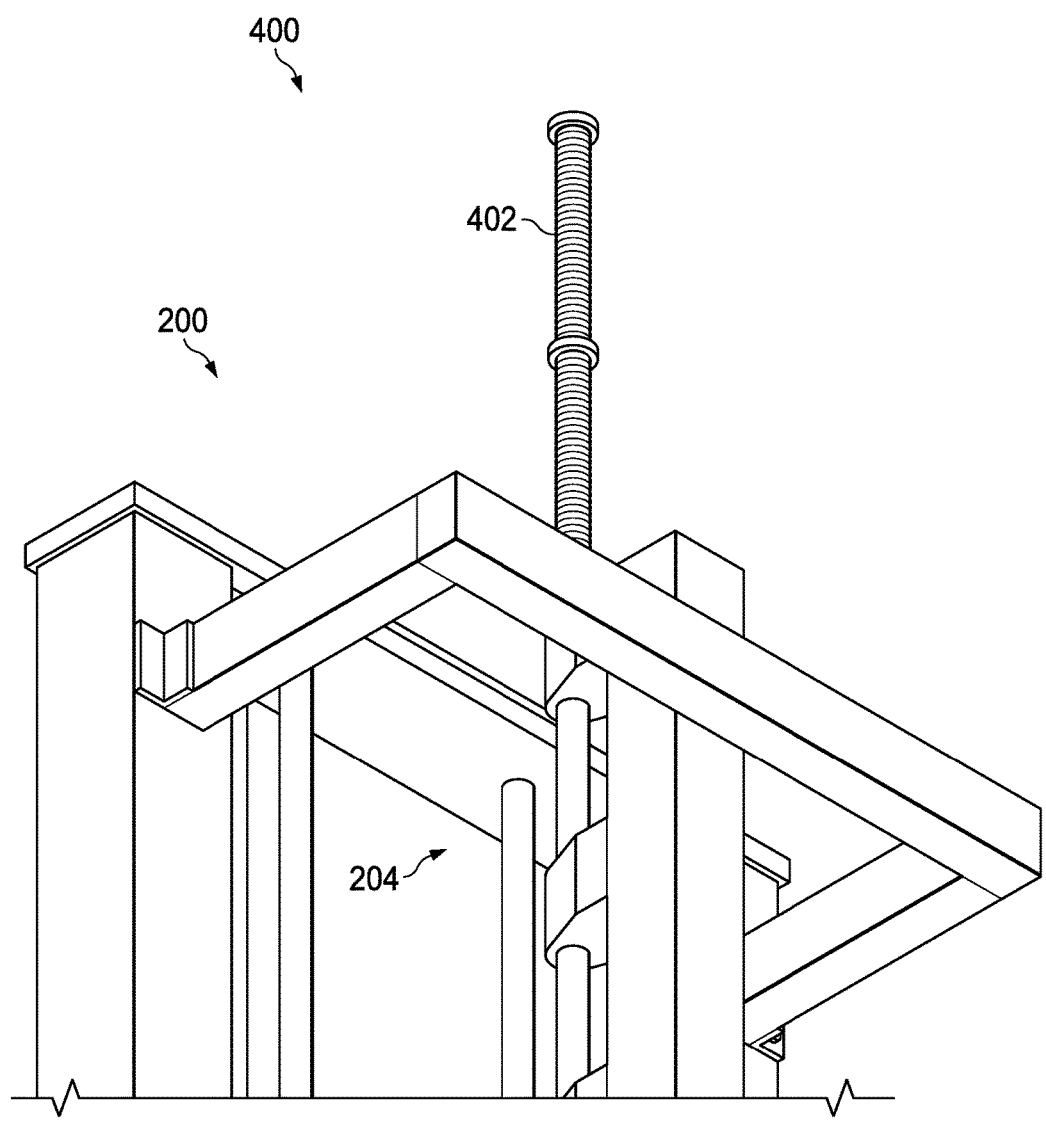
FIG. 4 is an illustration of an isometric view of a portion of a mechanical testing apparatus in accordance with an illustrative embodiment.

Turning now to FIG. 4, an illustration of an isometric view of a portion of a mechanical testing apparatus is depicted in accordance with an illustrative embodiment. View 400 of FIG. 4 is a view of mechanical testing apparatus 200 within box 4 of FIG. 2.

In view 400, spring 402 is visible. Spring 402 suspends Hopkinson bar 204 to avoid the gravity being applied to the tensile specimen before dynamic loading.

Figure 5:
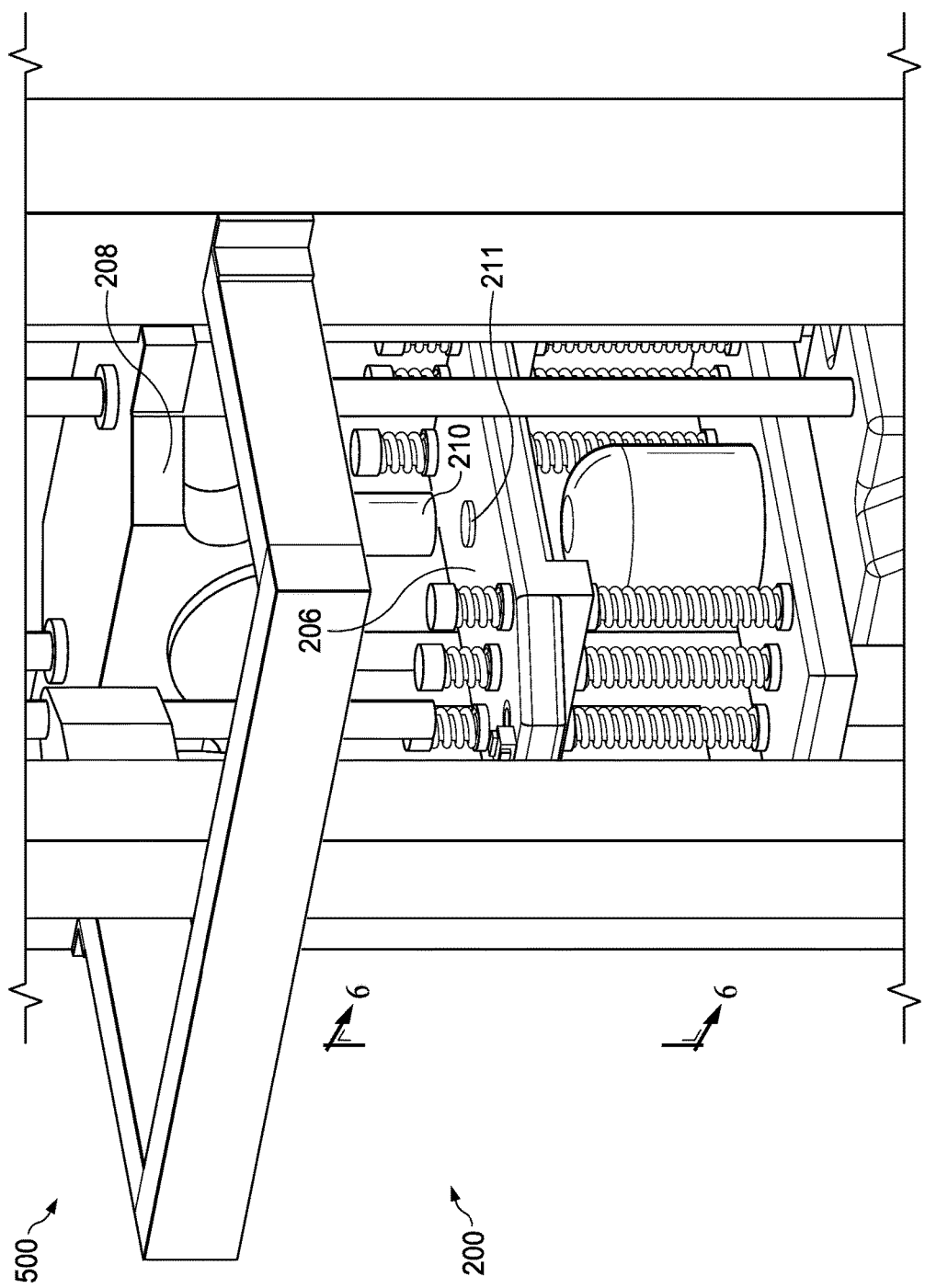
FIG. 5 is an illustration of a first side isometric view of an impact portion of a mechanical testing apparatus in accordance with an illustrative embodiment.

Turning now to FIG. 5, an illustration of a first side isometric view of an impact portion of a mechanical testing apparatus is depicted in accordance with an illustrative embodiment. View 500 of FIG. 5 is a view of mechanical testing apparatus 200 within box 5 of FIG. 2. View 500 is a view of the portion of drop table system 202 that generates a force on the specimen.

Upon the free drop of carriage 208, impactor 210 attached to the bottom of carriage 208 impacts impact plate 206 in its center. Impact plate 206 then transfers the impact load to a tensile specimen (not depicted) attached to impact plate 206 through threads. Such an impact load subjects the specimen in dynamic tension.

Figure 6:
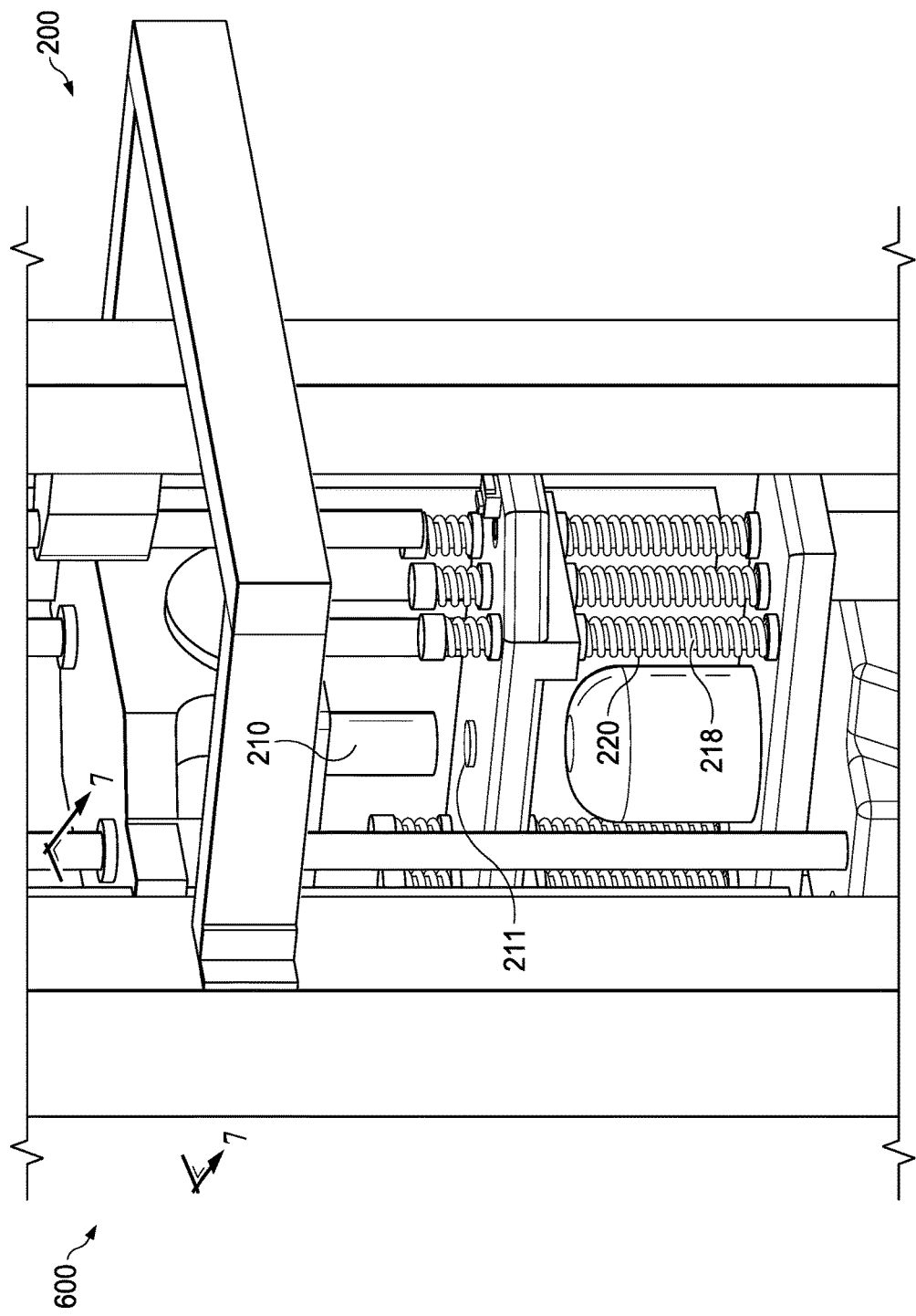
FIG. 6 is an illustration of a second side isometric view of an impact portion of a mechanical testing apparatus in accordance with an illustrative embodiment.

Turning now to FIG. 6, an illustration of a second side isometric view of an impact portion of a mechanical testing apparatus is depicted in accordance with an illustrative embodiment. FIG. 6 is a view of mechanical testing apparatus 200 from direction 6 of FIG. 5.

View 600 provides a closer view of impactor 210, plurality of guide rods 218, and plurality of springs 220. As depicted, impactor 210 is a one-inch diameter cylindrical steel impactor.

Figure 7:
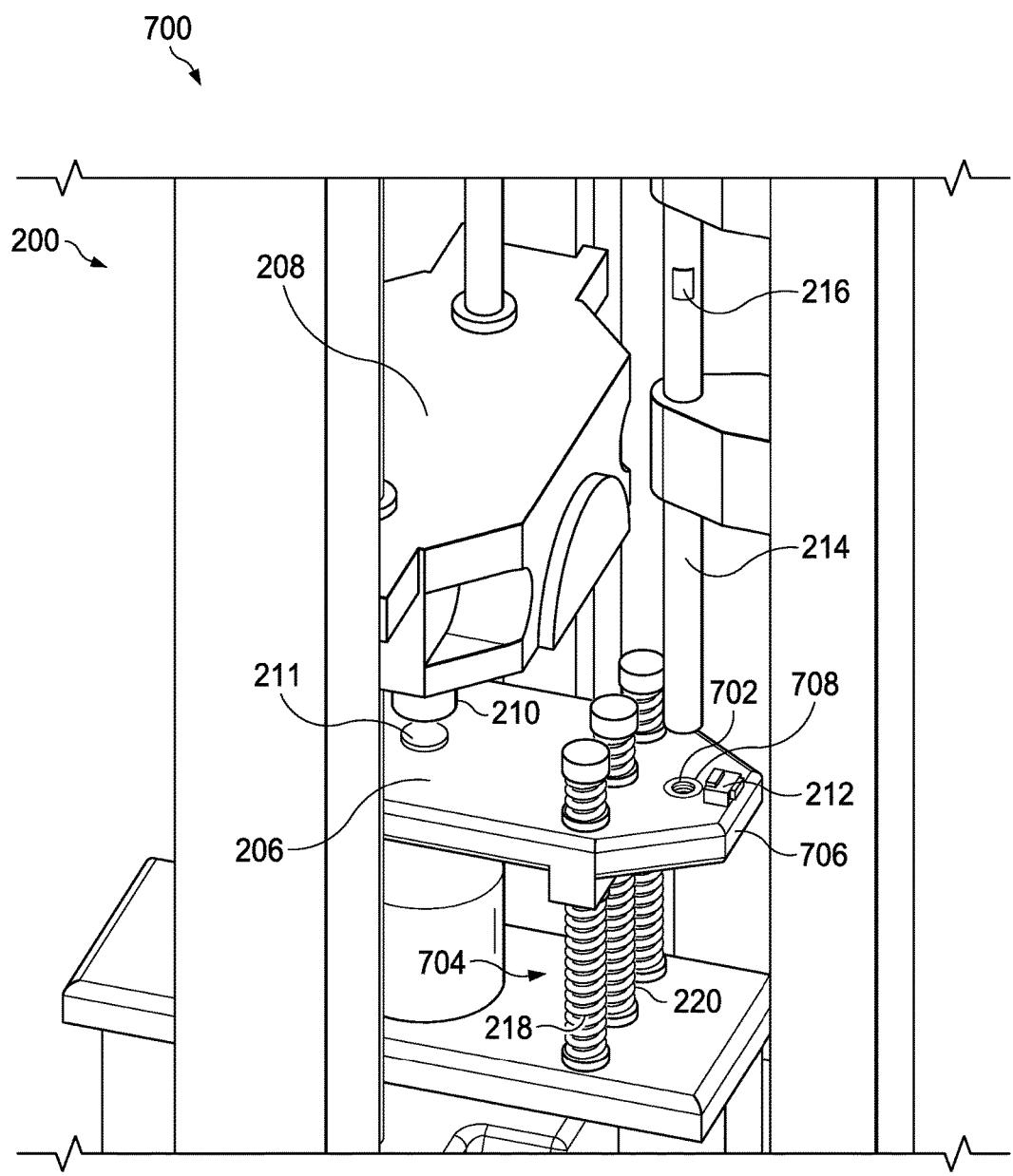
FIG. 7 is an illustration of a top isometric view of an impact portion of a mechanical testing apparatus in accordance with an illustrative embodiment.

Turning now to FIG. 7, an illustration of a top isometric view of an impact portion of a mechanical testing apparatus is depicted in accordance with an illustrative embodiment. View 700 of FIG. 7 is a view of mechanical testing apparatus 200 within box 5 from direction 7 of FIG. 6.

View 700 provides a closer view of accelerometer 212, number of strain gauges 216, and threaded hole 702 in impact plate 206. Number of strain gauges 216 is configured to measure strain in bar 214 during testing of a specimen. As depicted, number of strain gauges 216 is two gauges in this example.

A specimen (not depicted) would connect impact plate 206 to bar 214 during testing. More specifically, threaded hole 702 has ½"-20 threads and is located between guide rods 704 of plurality of guide rods 218 and edge 706 of impact plate 206. During operation, a tensile specimen will be threaded into threaded hole 702.

As depicted, threaded hole 702 is formed by insert 708 positioned within impact plate 206. Insert 708 may be secured within impact plate 206 using any desirable joining method. For example, insert 708 is threaded into impact plate 206 as depicted.

Figure 8:
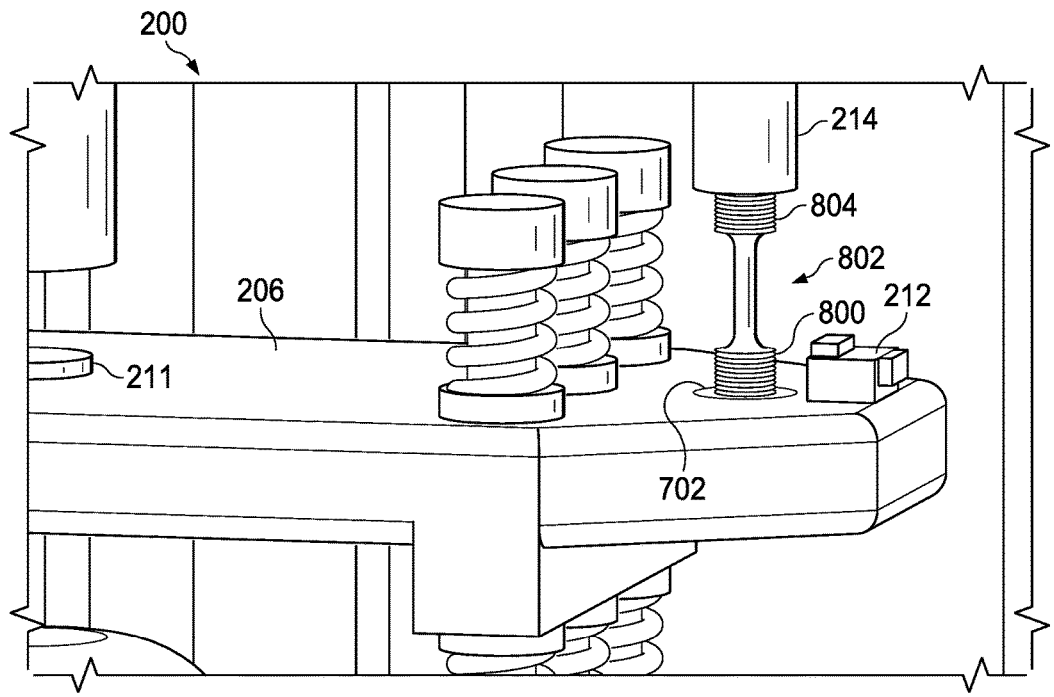
FIG. 8 is an illustration of a specimen within a mechanical testing apparatus prior to testing in accordance with an illustrative embodiment.
Figure 9:
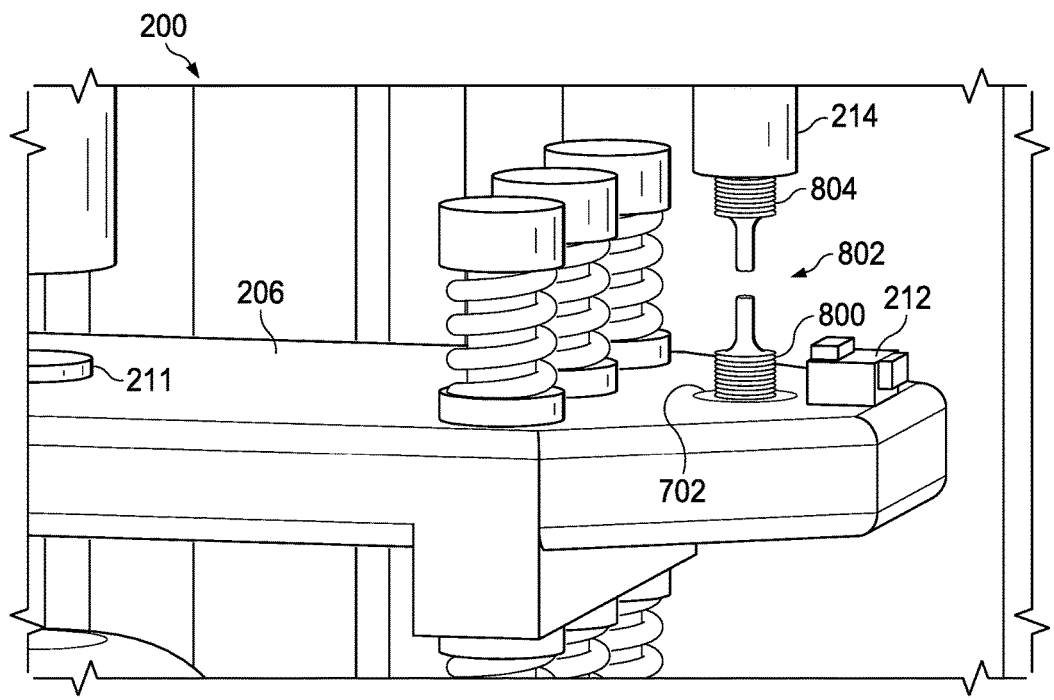
FIG. 9 is an illustration of a specimen within a mechanical testing apparatus after testing in accordance with an illustrative embodiment.

Turning now to FIGS. 8 and 9, an illustration of a specimen within a mechanical testing apparatus prior to and after testing is depicted in accordance with an illustrative embodiment. FIGS. 8 and 9 are views of a specimen within mechanical testing apparatus 200 of FIG. 2.

First end 800 of specimen 802 is threaded into threaded hole 702 of mechanical testing apparatus 200. Second end 804 of specimen 802 is threaded into the end of bar 214. FIG. 8 depicts specimen 802 attached to impact plate 206 and bar 214 before a test. FIG. 9 depicts specimen 802 attached to impact plate 206 and bar 214 after a test.

Figure 10:
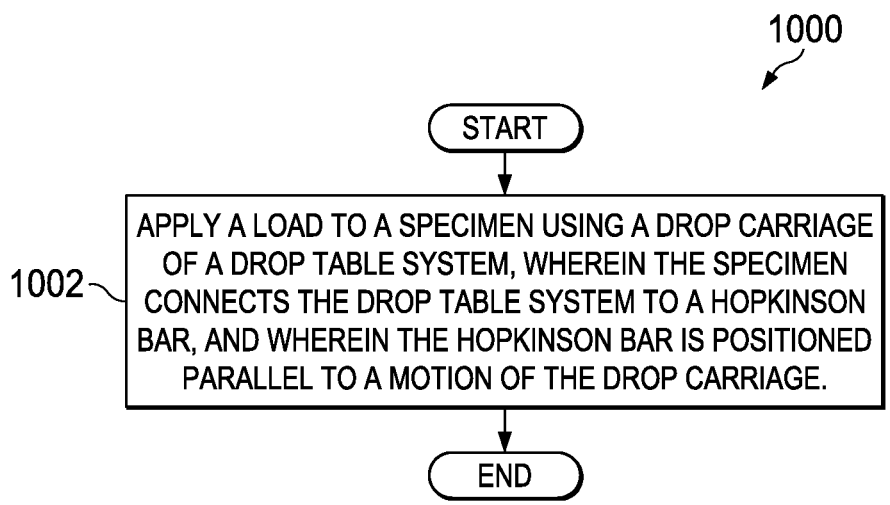
FIG. 10 is an illustration of a flowchart of a method of mechanically testing a specimen in accordance with an illustrative embodiment.

Turning now to FIG. 10, an illustration of a flowchart of a method for mechanically testing a specimen is depicted in accordance with an illustrative embodiment. Method 1000 may be used to mechanically test specimen 102 using mechanical testing apparatus 104. Method 1000 may be a method of using mechanical testing apparatus 200 of FIGS. 2-7.

Method 1000 applies a load to the specimen using a drop carriage of a drop table system, wherein the specimen connects the drop table system to a Hopkinson bar, and wherein the Hopkinson bar is positioned parallel to a motion of the drop carriage (operation 1002). Afterwards, the method terminates.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order depending upon the functionality involved. Also, other blocks may be added in addition to the illustrated blocks in a flowchart or block diagram.

In some illustrative examples of method 1000, applying the load comprises impacting the impact plate of the drop table system with an impactor connected to the drop carriage, and the impact plate has a threaded hole configured to hold a first end of the specimen.

In some illustrative examples of method 1000, the Hopkinson bar comprises a metal bar and number of strain gauges connected to the surface of the metal bar. Method 1000 may further comprise taking acceleration measurements using an accelerometer connected to the impact plate; taking strain measurements using the number of strain gauges; and determining at least one of a stress on the specimen or a strain on the specimen using at least one of the acceleration measurements or the strain measurements.

The illustrative embodiments provide a method and apparatus for mechanical property characterization of materials. The apparatus may be referred to as a "Dropkinson Bar." The Dropkinson Bar is configured to perform mechanical property characterization of materials at intermediate strain rates ranging from $10^1$ to $10^2$ s$^{-1}$. This new apparatus may also be utilized for mechanical testing at even higher strain rates in the order of $10^3$ s$^{-1}$. The Dropkinson Bar is configured to obtain intermediate-rate stress-strain data of materials that have not been available due to the lack of suitable experimental apparatus.

Conventional mechanical testing equipment has too high of a noise to signal ratio to be reliable. The Dropkinson Bar integrates drop table and Hopkinson bar test principles. By integrating drop table and Hopkinson bar test principles, more reliable and precise material characterization at intermediate strain rates is determined, which is out of working capability of either a sole drop table or a sole Hopkinson bar. This Dropkinson Bar bridges current quasi-static testing frame and conventional split Hopkinson bar tests, and provides potential for in-depth investigation of transition from quasi-static response to dynamic response of materials.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A mechanical testing apparatus for a specimen, the mechanical testing apparatus comprising:
   a drop table system having a drop carriage; and
   a Hopkinson bar positioned parallel to a motion of the drop carriage and connected to the drop table system by the specimen;
   wherein the drop table system comprises:
   an impact plate having a threaded hole configured to hold a first end of the specimen, wherein the drop carriage is configured to move towards the impact plate;
   an impactor connected to the drop carriage, the impactor configured to strike a pulse shaper associated with the impact plate;
   an accelerometer connected to the impact plate;
   a plurality of guide rods extending through the impact plate;
   a plurality of springs surrounding each of the plurality of guide rods;
   a bottom plate connected to the plurality of guide rods; and
   a bumper connected to the bottom plate, wherein the bumper is configured to absorb momentum and stop the impact plate.

2. The mechanical testing apparatus of claim 1, wherein the mechanical testing apparatus is configured to obtain a tensile stress-strain response of the specimen at intermediate strain rates in the order of $10^2$ s$^{-1}$.

3. The mechanical testing apparatus of claim 2, wherein the mechanical testing apparatus is further configured to obtain a tensile stress-strain response at higher or lower strain rates by varying an impact speed of the drop carriage of the drop table system.

4. The mechanical testing apparatus of claim 1, wherein the specimen has a threaded engagement with each of the drop table system and the Hopkinson bar.

5. The mechanical testing apparatus of claim 1, wherein a strain of the specimen is calculated as $$\varepsilon(t) = \int_0^t \dot{\varepsilon} dt = \int_0^t \frac{\int_0^t a(t) dt - C_0 \varepsilon_0(t)}{L_s} dt$$

wherein a(t) is an acceleration history recorded by the accelerometer; $C_0$ is a speed of an elastic stress wave in a material of the Hopkinson bar; wherein $$C_0 = \sqrt{\frac{E_0}{\rho_0}};$$

wherein $\rho_0$ is a density of the material of the Hopkinson bar; and $L_s$ is a gauge length of the specimen.

6. The mechanical testing apparatus of claim 1, wherein the Hopkinson bar comprises a metal bar and a number of strain gauges connected to a surface of the metal bar.

7. The mechanical testing apparatus of claim 6, wherein specimen stress is calculated as $$\sigma(t) = \frac{A_0}{A_S} E_0 \varepsilon_0(t),$$

wherein $A_0$ is a cross-sectional area of the Hopkinson bar, wherein $A_s$ is a cross-sectional area of the specimen, $E_0$ is a Young's modulus of the Hopkinson bar, and $\varepsilon_0$ is a bar strain recorded with the number of strain gauges.

8. The mechanical testing apparatus of claim 6, wherein the metal bar is suspended by a spring attached to a first end of the metal bar.

9. A mechanical testing apparatus for a specimen, the mechanical testing apparatus comprising:
a drop table system having a drop carriage; and
a Hopkinson bar positioned parallel to a motion of the drop carriage and connected to the drop table system by the specimen;
wherein the drop table system comprises:
an impact plate configured to hold the specimen;
a plurality of guide rods extending through the impact plate;
a plurality of springs surrounding each of the plurality of guide rods;
a bottom plate connected to the plurality of guide rods; and
a bumper connected to the bottom plate, wherein the bumper is configured to absorb momentum and stop the impact plate.

10. The mechanical testing apparatus of claim 9, comprising an accelerometer connected to the impact plate.

11. The mechanical testing apparatus of claim 9, wherein the specimen is threadably engaged with each of the drop table system and the Hopkinson bar.

12. The mechanical testing apparatus of claim 9, wherein the mechanical testing apparatus is configured to obtain a tensile stress-strain response of the specimen at intermediate strain rates in the order of $10^2$ s$^{-1}$.

13. The mechanical testing apparatus of claim 12, wherein the mechanical testing apparatus is further configured to obtain a tensile stress-strain response at higher or lower strain rates by varying an impact speed of the drop carriage.

* * * * *